United States Patent [19]

Kolb

[11] Patent Number: 4,527,569
[45] Date of Patent: Jul. 9, 1985

[54] DEVICE FOR GUIDING A SURGICAL NEEDLE INTO A BLOOD VESSEL

[75] Inventor: Peter J. Kolb, Cape Town, South Africa

[73] Assignee: South African Inventions Develop. Corp., Pretoria, South Africa

[21] Appl. No.: 551,724

[22] Filed: Nov. 15, 1983

[30] Foreign Application Priority Data

Nov. 26, 1982 [ZA] South Africa ................ 82/8736

[51] Int. Cl.³ .............................................. A61B 10/00
[52] U.S. Cl. .................................. 128/660; 128/24 A; 604/116
[58] Field of Search ............................. 128/660, 24 A; 73/625–626; 604/115, 116, 272

[56] References Cited

U.S. PATENT DOCUMENTS

| 2,968,302 | 1/1961 | Fry et al. | 128/24 A |
| 3,556,079 | 1/1971 | Omizo | 128/24 A X |
| 4,346,717 | 8/1982 | Hoerten | 128/660 |

OTHER PUBLICATIONS

Petzoldt, R. et al., "Puncture of Veins and Arteries Assisted by Ultrasound", UTS in Medicine & Biology, vol. 2, pp. 331-333, Pergamon 1976.
Mozersky, D. et al., "Doppler-Controlled Needle Director, A Useful Adjunct to Angiography", Technical Notes. *Radiology*, V109, Oct. 1973, pp. 221-222.
Goldberg, B. et al., "UTS Aspiration Biopsy Techniques", *Jrnl. Clin. Ultrasound*, V. 4 #2, Apr. 1976, pp. 141-151.

Primary Examiner—Kyle L. Howell
Assistant Examiner—Francis J. Jaworski
Attorney, Agent, or Firm—Ladas & Parry

[57] ABSTRACT

A device for guiding a surgical needle (N) carried by a mount (30) into a blood vessel comprises receiving and transmitting ultrasonic transducers (26, 28). The transducers are positioned so that there is a point of convergence between the axis of the ultrasonic beam produced by the transmitting transducer and the axis of the line of sight along which the receiving transducer receives reflected waves. The mount (30) can perform both rotational and translational movements and the path along which the needle (N) moves when pushed into the patient intersects said point of convergence. The transducers (26, 28) and the mount (30) are interconnected so that movements of the needle mount (30) result in the transducers (26, 28) moving towards or away from one another so as to shift the point of convergence so that it remains coincident with the path along which the needle moves. In a further form the position of the needle mount is determined optically or magnetically and an output signal produced. The output signal is used to excite a phased array of ultrasonic transducers the outputs of which are arranged to interfere constructively along a specific axis. This axis is shifted as the needle mount is moved thereby to maintain the desired point of intersection between the line of sight of the receiving transducer, the axis along which the needle moves during insertion, and the axis along which constructive interference is occurring.

7 Claims, 19 Drawing Figures

DEVICE FOR GUIDING A SURGICAL NEEDLE INTO A BLOOD VESSEL

This invention relates to a device for guiding a surgical needle into a blood vessel.

BACKGROUND TO THE INVENTION

It is sometimes difficult for a doctor to find a blood vessel into which he wishes to insert a surgical needle for the purpose of injecting a substance into the blood, for the purpose of withdrawing blood or for the purpose of inserting a catheter.

OBJECT OF THE INVENTION

The object of the present invention is to provide a device which enables a doctor to detect the position of a blood vessel and which thereafter assists in guiding the surgical needle into the blood vessel.

SUMMARY OF THE INVENTION

According to the present invention there is provided a device for guiding a surgical needle into a blood vessel which device comprises first ultrasonic transducer means for producing an ultrasonic beam, second ultrasonic transducer means spaced from the first transducer means and serving to receive reflected ultrasonic waves, the transducer means being such that there is a point of convergence between the axis of the ultrasonic beam produced by the first transducer means and the axis of the line of sight along which the second transducer means receives reflected waves, and means for mounting a surgical needle, the needle mounting means being such that the axis of a needle carried thereby intersects said point of convergence and is skew to the plane which contains said axis of the ultrasonic beam and said axis of said line of sight.

Said needle axis preferably intersects said plane midway between the transducer means.

In one form the device comprises a first ultrasonic transducer for transmitting an ultrasonic beam, a second ultrasonic transducer for receiving reflected ultrasonic waves, and means mounting the first and second transducers for movement towards and way from one another thereby to enable the distance between said point of convergence and the transducers to be varied.

The needle mounting means can desirably perform rotational movements which have the effect of changing the angle of attack of the needle with respect to the patient's skin and translational movements which move the needle towards and away from the transducer means.

The device can further include linkage means between said needle mounting means and the means mounting the first and second transducers, said linkage means displacing said transducers towards or away from one another when the needle mounting means is moved.

In another form the device comprises a phased array of ultrasonic transducers forming said first transducer means, and an ultrasonic transducer forming said second transducer means, means for detecting the attitude of said needle mounting means and for producing an output signal, and means for processing said output signal and feeding it to said phased array thereby to excite said phased array so that constructive interference between the wavelets occurs along an axis which intersects the point of convergence between the axis of a needle carried by the needle mounting means and the line of sight along which the said ultrasonic transducer receives reflected ultrasonic waves.

In this latter form the means for detecting the attitude of the needle mounting means can comprise a source of parallel light, a mirror carried by said needle mounting means for reflecting light along a path which shifts upon there being a change in the attitude of said needle mounting means, and a light sensitive optical array for detecting where the light reflected from said mirror impinges thereon and for producing an output signal in dependance on the detected point of impingement. Alternatively, the means for detecting the attitude of the needle mounting means can comprise magnetic means for producing an output signal in dependance on the detected attitude of the needle mounting means.

BRIEF DESCRIPTION OF THE DRAWINGS

For a better understanding of the present invention and to show how the same may be carried into effect, reference will now be made, by way of example, to the accompanying drawings in which.

DETAILED DESCRIPTION OF THE PREFERRED EMBODIMENT

Figure 1:
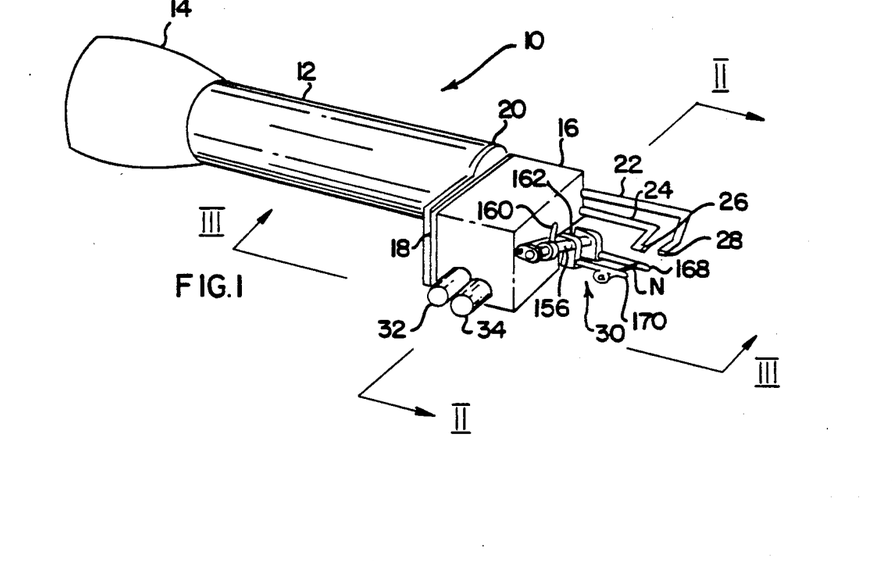
FIG. 1 is a pictorial view of an ultrasonic needle guide.

Referring firstly to FIG. 1, the ultrasonic needle guide illustrated is generally designated 10 and comprises a barrel 12 containing the electronic components and the batteries of the needle guide, a speaker 14 mounted at one end of the barrel 12, and a casing 16 at the other end of the barrel 12. A piece of double sided mirror tape, 18 lies between the casing 16 and the end plate 20 of the barrel 12.

Upper and lower transducer transport bars 22 and 24 protrude in both directions from the casing 16, there being transducers 26 and 28 mounted on the bars 22 and 24 respectively. One transducer acts as a transmitter and produces a pencil beam of ultrasound which, in use, is directed into the tissue of the patient, and the other transducer acts as a receiver for the reflected signal. Each transducer is constituted by a piece of piezo-electric material as will be described in more detail hereinafter.

A mounting structure for the needle which is to be guided into the blood vessel is shown at 30. Two rotatable, knurled control knobs are shown at 32 and 34, these protruding rearwardly from the casing 16. The structure 30 lies on the side of the casing 16 remote from the barrel 12.

Figure 3:
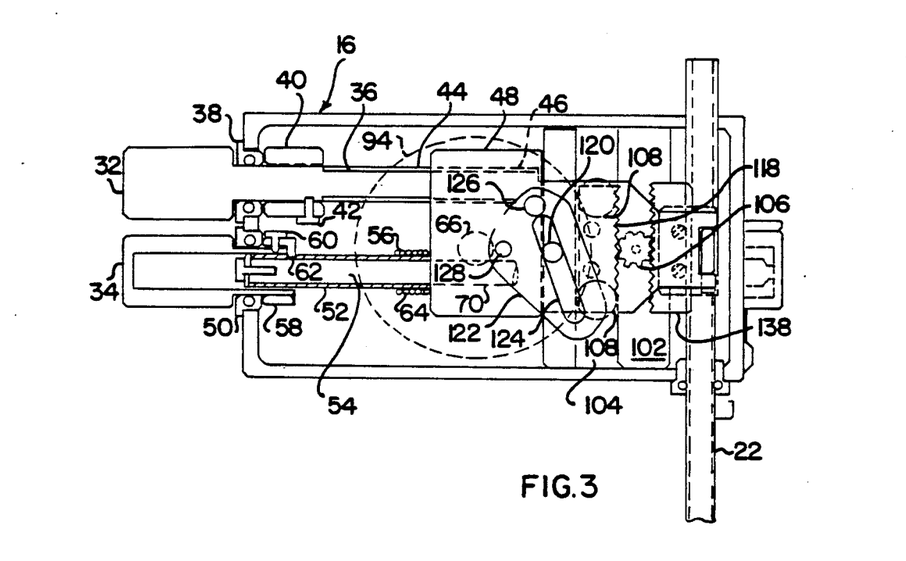
FIG. 3 is a top plan view of the mechanical components of FIG. 2.

Referring now to FIG. 3, the knob 32 is integral with a shaft 36 which passes through a bearing bush 38 mounted in the rear wall of the casing 16. A collar 40 is secured by a grub screw 42 to the shaft 36 and prevents axial movement of the shaft 36. The end portion 44 of the shaft 36 is threaded, and this end portion is screwed into a tapped bore 46 of a block 48.

The knob 34 (FIGS. 2 and 3), which has a blind bore therein, passes through a bearing bush 50. An elongate clutch sleeve 52 extends from adjacent the face of the block 48 and into the blind bore of the knob 34, there being a drive shaft 54 within the sleeve 52. The sleeve 52 is formed with a longitudinally extending slot 56 (FIG. 3).

Figure 2:
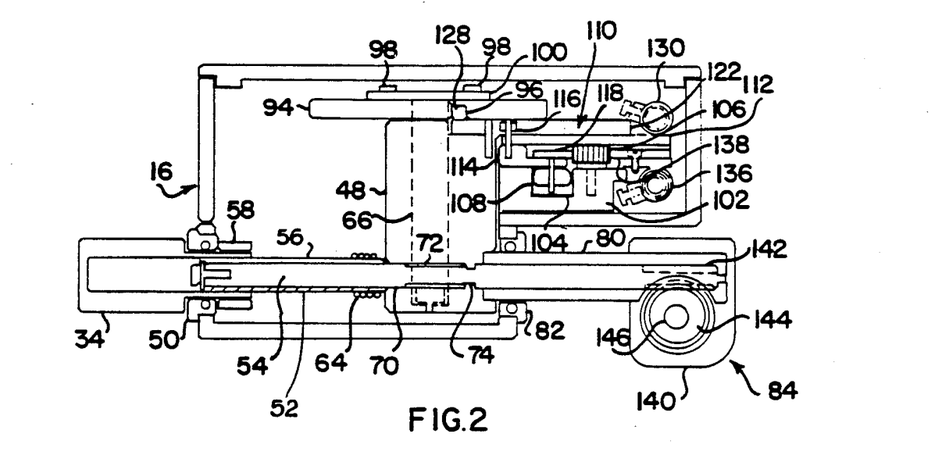
FIG. 2 is a side elevation of some of the mechanical components of the needle guide of FIG. 1.

A clutch collar 58 is secured by a grub screw 60 to the knob 34, the collar 58 having an inward projection 62 which is entered in the slot 56 of the sleeve 52. A number of 'Circlips' 64 are placed around the sleeve 52 adjacent the block 48 to close-up the longitudinally split sleeve 52. Rotation of the knob 34 is transmitted to the shaft 54 by way of the collar 58, the projection 62 and the sleeve 52. The 'Circlips' 64 ensure that the frictional engagement between the shaft 54 and the longitudinally split sleeve 52 is sufficient to transmit such drive. Should, however, the mechanism being driven by the shaft 54 (and which will be described in more detail hereinafter) reach the end of its travel or stick, then the sleeve 52 slips on the shaft 54 to prevent damage to this mechanism.

Figure 4:
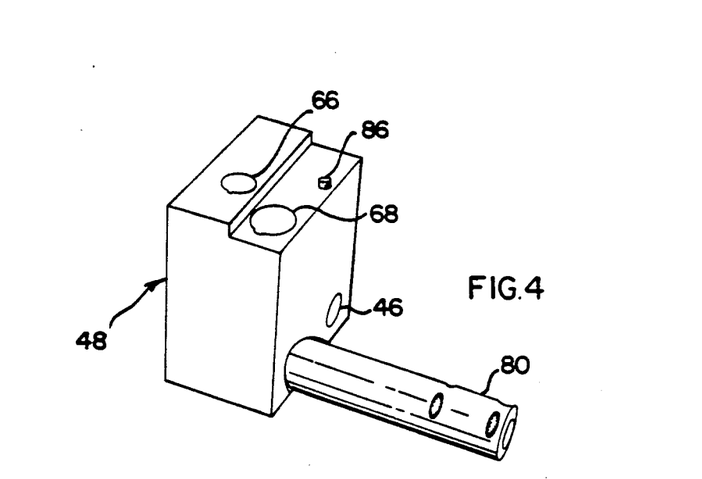
FIG. 4 is a pictorial view of a block.
Figures 5, 6:
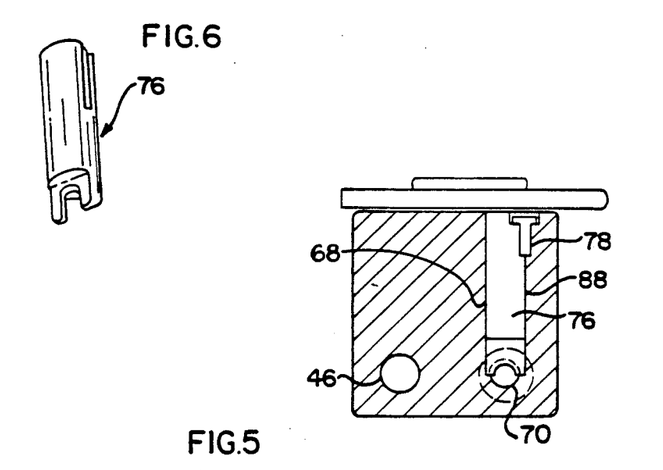
FIG. 5 is a section through the block of FIG. 4, FIG. 5 showing components in addition to the block.
FIG. 6 is a pictorial view of a retaining clip.

Referring now to FIGS. 4 and 5 as well as FIGS. 2 and 3, the block 48 has a vertical bore 66 which, as will be described in more detail hereinafter, receives the shaft of a scroll. The block 48 also has a second vertical bore 68 (FIGS. 4 and 5) and a second horizontal bore 70 which is parallel to the bore 46. The bore 66 intersects the bore 70 tangentially (FIG. 3) and the bore 68 extends vertically from the bore 70 as best seen in FIG. 5. The bore 68 is not shown in FIGS. 2 and 3.

The part of the shaft 54 which is within the bore 70 is formed with a worm 72 (FIG. 2) and with a circumferential groove 74. A retaining clip 76 (FIG. 6) having a U-shaped lower end is inserted into the bore 68 from above and its U-shaped lower end fits in the groove 74. The clip 76 thus prevents any axial movement of the shaft 54. A screw 78 extending parallel to the clip 76 (FIG. 5) retains the clip 76 in the bore 68. The screw 78 is in a tapped bore formed partly in the clip 76 and partly in the block 48.

A sleeve 80 is soldered or otherwise secured to the face of the block 48 co-axial with the bore 70. The sleeve 80 passes through a sealing bush 82 mounted in the front wall of the casing 16. The shaft 54 passes through the block 48 and the sleeve 80. A gear structure 84, which will be described in more detail hereinafter, is mounted at the forward end of the sleeve 80.

The final features of the block that should be noted are firstly that its upper surface is stepped thereby to provide two surface portions which lie in different horizontal planes and that a guide rail platform pivot pin 86 extends upwardly from the lower of the two surface portions of the block 48.

Figure 7:
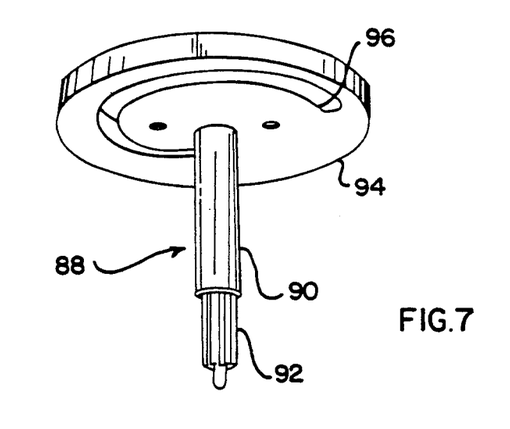
FIG. 7 is a pictorial view of a scroll.

A scroll 88 is illustrated in FIG. 7 and comprises a shaft 90 the lower end portion of which is in the form of a pinion 92. The shaft 90 is secured to a scroll disc 94 and a curving groove 96 is cut into the lower face of the disc 94. The pinion 92 co-operates with the worm 72 cut on the shaft 54.

The shaft 90 and disc 94 of the scroll 88 are separate components and are secured together by two small screws 98 (FIG. 2) which pass through an enlarged head 100 at the upper end of the shaft 90. The screws 98 pass through arcuate slots (not shown) in the head 100 so that the shaft 90 can be rotated with respect to the scroll disc 94 and then re-secured in its adjusted position. The scroll disc 94 has only been shown as a dashed circle in FIG. 3 to avoid obscuring other detail.

A rail 102 which has an upwardly open channel 104 therein extends from one side of the casing 16 to the other forwardly of the block 48. A pinion 106 is mounted on the top face of the rail 102.

Within the channel 104 there is a pair of rollers 108 which are mounted on the underside of a linking plate structure generally designated 110. The rollers 108 can, if desired, be replaced by blocks which slide in the channel 104.

The linking plate structure 110 comprises a linking plate 112 and an element 114 secured by screws 116 to the underside of the plate 112. The rollers 108 are mounted on the underside of the element 114. A rack 118 is secured between the plate 112 and the element 114, this rack co-operating with the pinion 106.

A small roller 120 (FIG. 3) is mounted on the top face of the linking plate 112.

A guide rail platform 122 is located beneath the scroll disc 94 and above the linking plate 112. The guide rail platform 122 has an elongate slot 124 (FIG. 3) and a blind bore 126 in the underside thereof and an upwardly projecting pin 128 on the top surface thereof. The blind bore 126 receives the pin 86 of the block 48 thereby pivotally mounting the platform 122 on the block. The roller 120 is received in the slot 124 and the pin 128 enters the groove 96 in the underside of the scroll disc 94.

Figure 8:
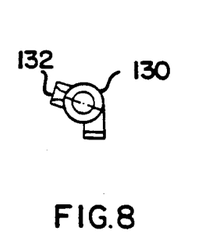
FIGS. 8 and 9 illustrate the transport sleeve of the upper transducer bar.
Figure 9:
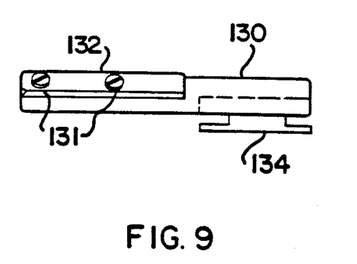

The linking plate 112 has its forward end connected to a sleeve 130 (see also FIGS. 8 and 9) through which the upper bar 22 passes. The sleeve 130 has an element 132 soldered thereto to make its outer periphery non-symmetrical in section. The sleeve 130 and element 132 slide in an aperture of corresponding shape in the side wall of the casing 16 and extend across the gap between the casing 16 and the end plate 20 to enter the barrel 12. The sleeve 130 is secured to the upper bar 22 by means of grub screws 131. When these grub screws are loosened, the bar 22 can be turned in the sleeve 130 thereby to adjust the angular position of the tranducer 26. The T-shaped protrusion 134 of the sleeve 130 defines two slots into which the forked end of the plate 112 fits.

Figure 10:
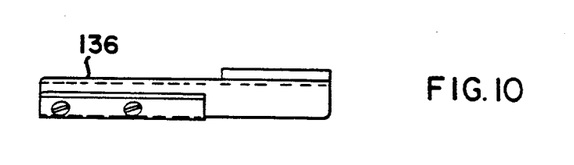
FIGS. 10 and 11 illustrate the transport sleeve of the lower transducer bar.
Figure 11:
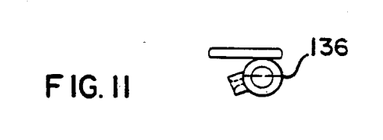

The lower bar 24 is similarly within a sleeve 136 (FIGS. 10 and 11) which is constructed in the same way as the sleeve 130 and is thus likewise of non-symmetrical cross sectional shape. The sleeve 136 slides in an aperture of corresponding shape in the wall of the casing 16. A rack 138 (FIGS. 2 and 3) is secured to a rack support of the sleeve 136 and meshes with the pinion 106.

Figure 12:
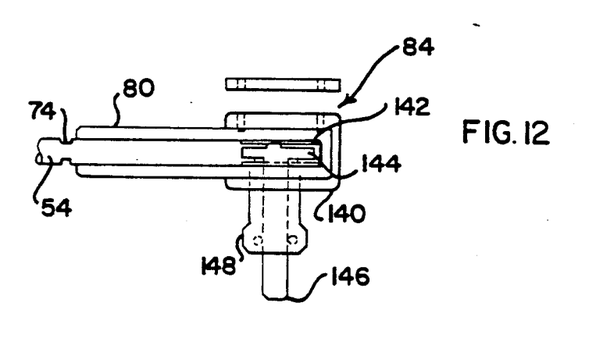
FIG. 12 illustrates a gear structure.

The gear structure 84 comprises a housing 140 (FIG. 12) located beneath the overhanging part of the casing 16, the housing 140 being secured to the forward end of the sleeve 80. The shaft 54 is, at its forward end, in the form of a worm 142 which meshes with a gear 144. The gear 144 is rotatably mounted within the housing 140 and is fast with a shaft 146. The shaft 146 is rotatable within a sleeve 148 which is itself secured to the side of the housing 140.

Figure 13:
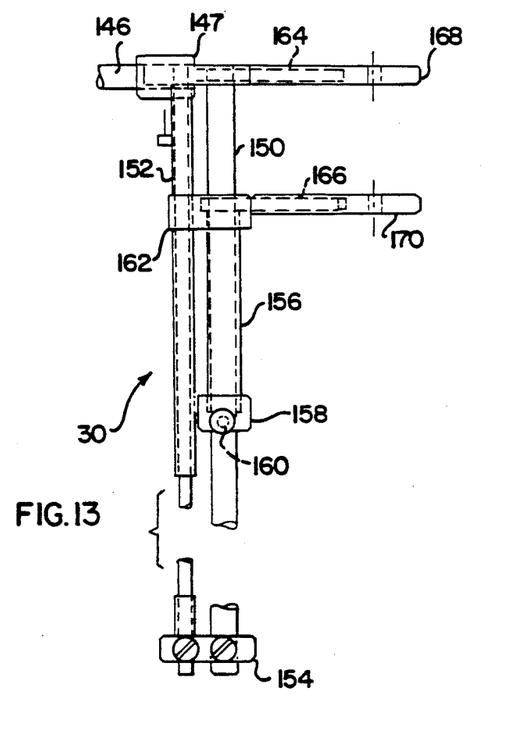
FIG. 13 illustrates a needle mounting structure.

The mounting structure 30 shown in FIG. 1 is illustrated in more detail in FIG. 13. On to the shaft 146 is mounted an anchor plate 147, a pair of parallel rods 150 and 152 being secured to the plate 147. At their rear ends the rods 150 and 152 are secured to a further plate 154, the plates 148 and 154 ensuring that the rods 150, 152 remain parallel.

The rod 150 passes through a guide sleeve 156 which is free to move along the rod 150. The sleeve 156 includes a collar 158 with an elongate grub screw 160 projecting upwardly therefrom. By tightening the grub screw 160 onto the rod 150, the sleeve 156 can be immobilised.

To prevent rotation of the sleeve 156 on the rod 150, the sleeve 156 is extended laterally by a plate 162 which has a slot cut in it through which the rod 152 passes with little clearance. The upper and lower bounding surfaces of this slot, by co-operating with the rod 152, prevent rotation of the guide sleeve 156.

Stub shafts 164 and 166 protrude from the plates 147 and 162 respectively, the stub shafts 164 and 166 being parallel to one another. Two sleeves 168, 170 of synthetic plastics material are, immediately prior to use of the device, pushed onto the stub shafts 164, 166. These sleeves 168, 170 have holes in them to receive the needle N (FIG. 1). The sleeves 168, 170 are weakened by means of notches in their walls at the regions of the needle holes.

The final mechanical portion which need be described is the mounting of the transducers 26, 28 on the bars 22, 24 respectively. In this regard reference is made to FIG. 14 in which reference numeral 172 designates a transducer housing which is in the form of a piece of square section brass. The housing 172 is soldered to a stainless steel ball 174 which is itself at one end of the bore of a short cylinder 176. The cylinder 176 is secured to the bar 22, 24. The bore is tapered at one end to form a seat for the ball 174. A screw 178 in the bore of the cylinder 176 clamps the ball in place. It will be understood that, to adjust the position of the housing 172, the screw 178 is loosened and the ball rotated in any direction within the cylinder 176.

Figure 14:
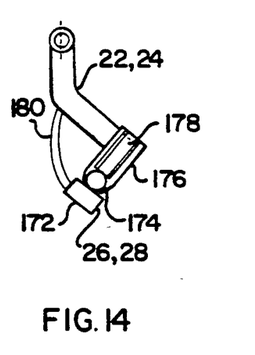
FIG. 14 illustrates the mounting of a transducer.

The piezoelectric crystal itself is in the form of a block which is 2 mm $\times$ 2.5 mm in edge dimensions and 0.2 mm thick. Two 38 gauge wires are soldered one to each face of the block and to a screened cable 180 which leads into the associated bar 22, 24 and extends through the bar 22, 24 into the barrel 12 for connection to the electronic system of the needle guide. The piezoelectric block is secured by adhesive to a polystyrene block and the composite polystyrene/piezoelectric block is pushed into the housing 172 and glued in place.

Piezoelectric crystals of the type designated LTZ5 were used. Philips crystals PZT5 and PZE5 can also be used.

Figure 15:
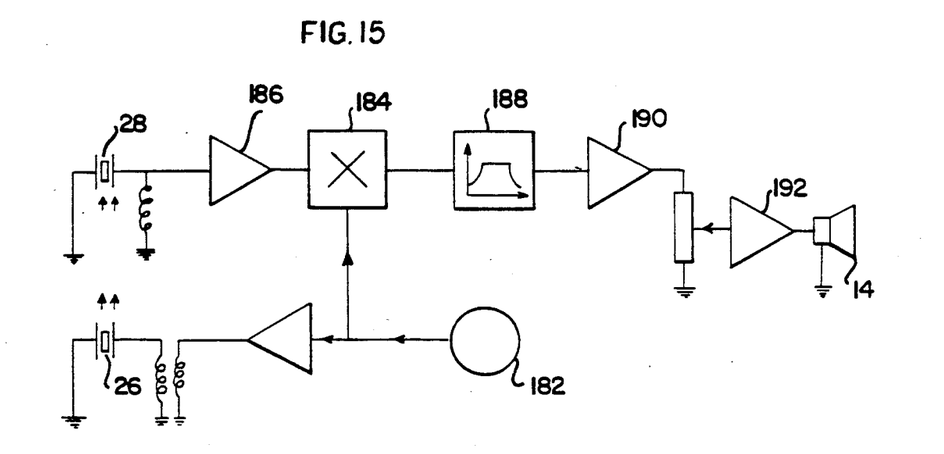
FIG. 15 is a block diagram of an electronic circuit.

A block diagram of the electronic circuit used is shown in FIG. 15. An oscillator 182 drives the transmitting transducer 26 and part of the output of the oscillator is fed to a mixer 184. A frequency of 9.0 MHz was chosen, this being the resonance frequency of the transducers. The mixer 184 also receives the signal from the receiving transducer 28 via an r.f. amplifier 186. The output of the mixer 184 is a product of the two input signals mentioned.

The output of the mixer is fed to a bandpass filter 188 which eliminates any r.f. signals as well as any low frequency signals derived from movement of the transducers on the patient's skin. The output from the filter 188 is fed via a logarithmic amplifier 190 and a power amplifier 192 to the speaker 14.

Before describing the operation of the ultrasonic needle guide, it should be mentioned that it operates on the Doppler principle. The transmitting transducer is excited by the fixed frequency oscillator 182, application of this frequency to the piezoelectric material causing it to vibrate and transmit a pencil beam of ultrasound at the blood vessel. The receiving transducer receives reflections from stationary parts of the patient's body in the region of the blood vessel that it is desired to locate and also receive signals reflected by the moving blood itself. The signals returned from the stationary parts of the patient are at the same frequency as the frequency applied to the transmitting transducer. However, signals reflected from the moving blood have a different frequency because of the Doppler shift.

A sterile cartridge comprising the two sleeves 168, 170 and a needle N pushed through the holes in the sleeves 168, 170 is first attached to the mounting structure 30. This is achieved by pushing the sleeves 168, 170 onto the stub shafts 164, 166.

When the knob 32 is rotated, the block 48 is displaced in a fore or aft direction depending on the direction of rotation of the knob. Movement of the block 48 results, of course, in motion of the sleeve 80 which in turn displaces the gear structure 84 linearly. The shaft 54 and sleeve 52 slide within the blind bore of the knob 34.

Motion of the block 48 results in a thrust or a pull being exerted on the platform 122 by virtue of the connection between the blind bore 126 and the pin 86 mounted on the block 48. Co-operation between the slot 124 and the roller 120 mounted on the linking plate 112 causes the linking plate structure 110 to move laterally, such movement being guided by the rollers 108 which are in the channel 104. Displacement of the linking plate structure results in displacement of the rack 118 which in turn results in rotation of the pinion 106. It will be understood that, as a result of rotation of the pinion 106, the rack 138 moves in the opposite direction to the rack 118.

Motion of the block 48 to the left in FIG. 3 results in movement of the linking plate structure 110 from the 'top' of the Figure towards the 'bottom'. As the plate 112 is directly connected to the upper bar 22, the bar 22 moves in the same direction. The bar 24 obviously moves in the opposite direction. Thus the transducers 26, 28 move away from one another.

It will be understood that the point of convergence C (FIG. 16) between the beam of ultrasound emitted by the transducer 26 and the 'line of sight' of the receiving transducer 28 moves further from the transducers as they move apart. Thus moving the transducers apart is an adjustment made to try and locate a blood vessel lying fairly far beneath the patient's skin.

Figure 16:
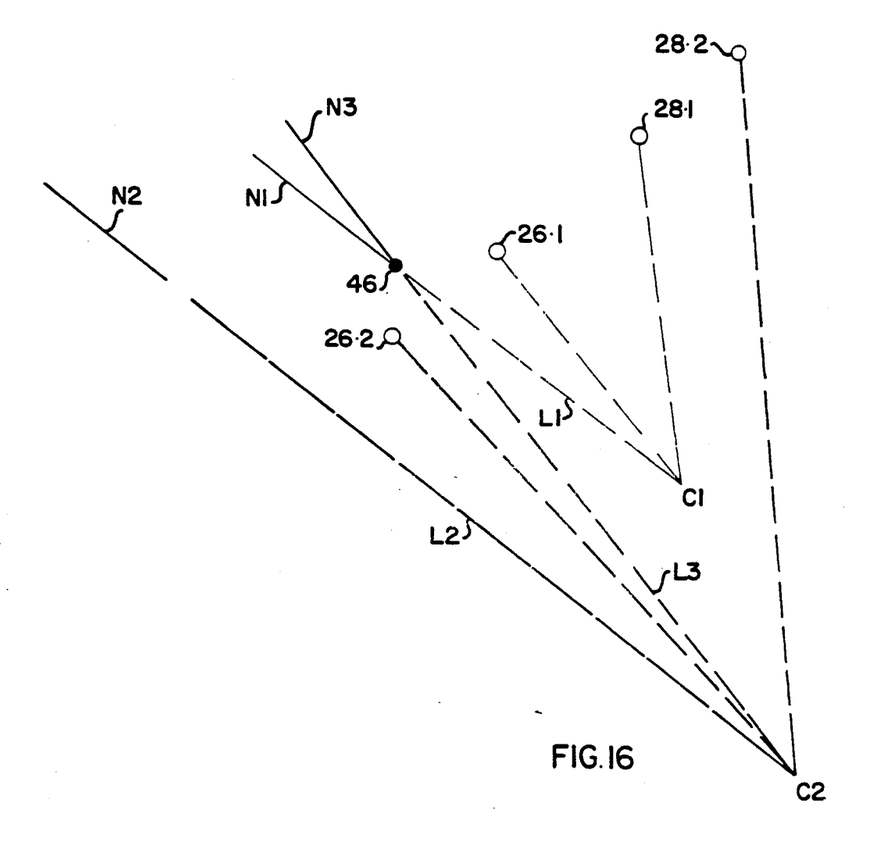
FIG. 16 is a diagrammatic representation illustrating the manner in which the ultrasonic needle guide operates.

This will best be understood by reference to FIG. 16 which shows the transducers at positions 26.1 and 28.1. Said point of convergence is at C1 and the needle lies at N1. The line along which the needle moves in the holes in the sleeves 168, 170 is shown at L1. If, due to movement of the block 48 when the knob 32 is rotated, the transducers move to positions 26.2 and 28.2, the point of convergence moves to C2. Rearward movement of the block 48 is accompanied by rearward movement of the structure 30. This movement is purely one of translation and has no rotational component. Thus the needle moves parallel to itself to N2 and its line of movement L2 intersects C2. Thus, if the user of the instrument has decided to insert his needle at a shallow angle, this angle is maintained regardless of the spacing between the transducers which is brought about by adjustment of the knob 32. Separation of the transducers from the positions 26.1, 28.1 to 26.2, 28.2 because the blood vessel is deeper than expected, results in rearward movement of the structure 30 and, as explained, this ensures that the needle remains pointed at the convergence C2 between the pencil beam of ultrasound and the line of sight to the receiving transducer without changing its angle of attack.

It will be appreciated from the preceding description with reference to FIG. 16 that, as the structure 30 is moved rearwardly, the point at which the needle enters the patient moves away from the area at which the beam of ultrasound is penetrating the patient. If it is decided that the point of entry should be close to this area, then the needle must be inserted at a steeper angle.

When the knob 34 is rotated, drive is transmitted to the shaft 54 and thence by way of the worm 72, pinion 92 and shaft 90 to the scroll disc 94. Likewise, drive is transmitted via the worm 142 and gear 144 to the shaft 146. As the plate 147 is fast with the shaft 146, it will be understood that the entire structure 30 pivots about the axis of the shaft 146.

Rotation of the scroll disc 94 causes the platform 122 to pivot about the pivotal connection constituted by the pin 86 and the blind bore 126. More specifically, as the scroll disc 94 turns the effective radius of the groove 96 at the point where the pin 128 lies varies. Thus the pin 128 is either drawn towards the axis of the bore 66 or moved away from it. Pivotal motion of the platform 122 results. Co-operation between the slot 124 of the pivoting platform 122 and the roller 120 causes displacement of the linking plate structure 110 transversly along the rail 102 with the same result as described above i.e. the transducers 26, 28 are moved towards or away from one another.

It will be understood that as the transducers are moved apart, said point of convergence moves further from them (from C1 to C2 in FIG. 16). Consequently, the arrangement of the parts is such that the gear 144 rotates clockwise as illustrated in FIG. 2 as the transducers 26, 28 are moved apart. This increases the angle of attack between the needle N and the patient's skin but does not move the needle away from the transducers. Thus the needle rotates from position N1 to N3 but does not move laterally.

When the instrument is switched on by a manually operable switch (not shown) the transducer 26 is excited by the oscillator 182 and emits the pencil beam of ultrasound. The user of the implement, using his medical knowledge to determine roughly where the vessel that he wishes to penetrates lies, adjusts the knobs 32, 34 until he has appoximately the angle of entry that he requires and approximately the correct depth of said point of convergence. He then displaces the needle guide over the patient's skin adjusting both the knobs 32 and 34, or one of them only, until the intensity of the sound of flowing blood emerging from the speaker is at a maximum. He knows then that said point of convergence is in the blood vessel.

He then pushes on the needle N to displace the sleeve 156 along the rod 150. When the needle is in the vessel or embedded to the point where it cannot thereafter easily be deflected from its line of travel, the sleeves 168, 170 are broken at their weak points. The needle and the needle guide are then free of one another and the needle guide can be removed. In cases where long needles are being used, the user can then push the needle into the patient sufficiently far to reach the blood vessel.

Figure 17:
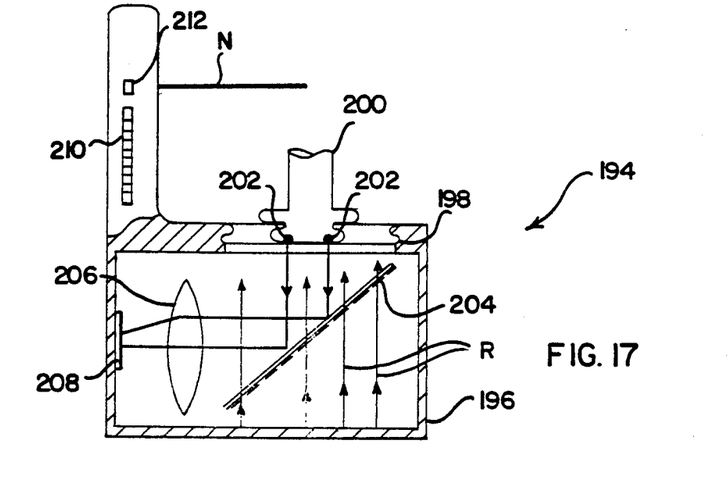
FIG. 17 is a diagrammatic representation of a further form of ultrasonic needle guide.

The needle guide diagrammatically illustrated in FIG. 17 is designated 194 and comprises a housing 196 having an elongate slot 198 in one wall thereof. A needle mount 200 clips into, and is movable along, the slot 198 and carries two mirrors 202.

A one-way mirror 204 lies beneath the slot 198 and there is a source (not shown) of parallel light. An optical focussing system 206 lies between the mirror 204 and an optical array 208. This optical array can be, for example, that manufactured under the designation IS32 Optic RAM by Micron Technology Inc. of Boise, Id., USA. The parallel rays R from the light source pass through the mirror 204 and are reflected as two points of light from the mirrors 202 onto the reflective surface of the mirror 204. The system 206 focusses the two light points onto the optical array 208.

It will be understood from the above description that the position of the needle mount 200 determines the position of the points of light on the array 208. These points shift if the mount is moved along the groove or is rotated in the groove. By suitable analysis of the output of the array 208, preferably using a microprocessor, a signal can be created which is unique to the position occupied by the needle mount 200.

Figure 19:
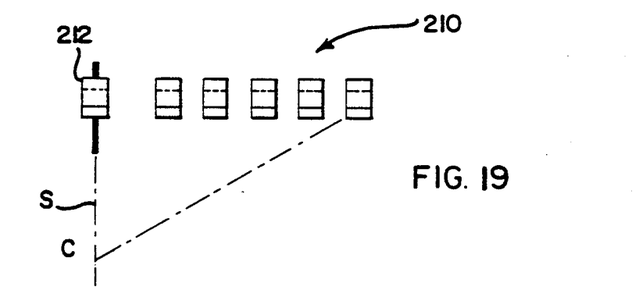

The needle guide 194 further includes a phased array of ultrasonic transducers designated 210 in FIGS. 17 and 19 and single ultrasonic transducer 212. The array 210 serves as a transmitter and the transducer 212 is a receiver of reflected signals. In contradistinction to the embodiment of FIGS. 1 to 16, the array 210 and the transducer 212 are both stationary. By suitably exciting the array 210 it is possible to cause the individual wavelets to interfere constructively along one axis and destructively elsewhere. Thus the array 210 produces a pencil beam of ultrasound which can be shifted by changing the excitation of the array 210.

The geometry of the needle guide is such that the line of sight S (FIG. 18) of the transducer 212 and the axis of the needle N lie in the same plane, the path P along which the needle N moves intersecting the line of sight of the transducer 212.

The user of the needle guide, employing his medical knowledge, positions the array 210 and the receiving transducer 212 against the patient's skin (PS in FIG. 18) and over the zone where he believes the blood vessel which he requires the needle N to enter will lie. He then sweeps the transducer 212 laterally to and fro. At the same time the array 210 is switched into a scanning mode. In this mode the array is excited in such a way that the point of convergence oscillates in depth many times per second. An increase in the output level of the speaker of the needle guide as the transducer 212 passes over the blood vessel serves to indicate that, at that moment, the vessel lies in the plane which contains both the axis of the needle N and the line of sight of the transducer 212.

Figure 18:
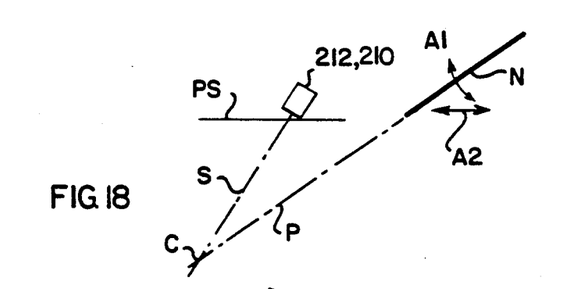
FIGS. 18 and 19 illustrate the method of operation of the guide of FIG. 17.

The user then switches off the scanning mode and varies either or both the angle of attack of the needle N with respect to the patient's skin PS or the position of the needle N with repect to the transducer 212. In FIG. 18 these possible movements are designated by arrows A1 and A2. Both movements have the effect of shifting the point of convergence C towards or away from the surface PS. Variation of the angle of attack as shown by arrow A1 results in rotation of the needle mount 200. Translational movement in the direction of arrow A2 shifts the mount 200 along the slot 198. Hence the points of light move over the array 208, so that its output changes. This varies the excitation of the array 210 and the axis along which constructive interference takes place shifts so that it is always directed at the point of convergence C. Immediately convergence point C lies within the blood vessel, the doppler effect of the flowing blood is detected due to the change in output of the speaker.

If desired the position of the needle mount 200 can be determined magnetically, or directly by means of position transducers such as potentiometers, variable capacitors or variable inductors.

I claim:

1. A device for guiding a surgical needle into a blood vessel which device comprises first ultrasonic transducer means for producing an ultrasonic beam, second ultrasonic transducer means spaced from the first transducer means and serving to receive reflected ultrasonic waves, the transducer means being orientated such that there is a point of convergence between the axis of the ultrasonic beam produced by the first transducer means and the axis of the line of sight along which the second transducer means receives reflected waves, means for mounting the first and second transducer means for relative movement thereby to enable the distance between said point of convergence and the transducer means to be varied, means for mounting a surgical needle, and linkage means between said needle mounting means and the means for mounting the first and second transducer means, said linkage means displacing said transducer means relative to one another when the needle mounting means is moved, relative displacement of the transducer means being in such manner that the axis of a needle carried by the needle mounting means continuously intersects said point of convergence and is skew to the plane which contains said axis of the ultrasonic beam and said axis of said line of sight.

2. A device according to claim 1 and including a casing by which said needle mounting means and said means mounting the first and second transducer means are carried, there being drive means for shifting said needle mounting means in a translational movement with respect to the casing.

3. A device according to claim 1, and including a casing by which said needle mounting means and said means mounting the first and second transducer means are carried, there being drive means for rotating said needle mounting means with respect to the casing.

4. A device according to claim 1 and including a casing by which said needle-mounting means and said means mounting the first and second transducer means are carried, there being drive means for shifting and for rotating said needle mounting means in a translational rotational movement with respect to the casing.

5. A device for guiding a surgical needle into a blood vessel which device comprises a phased array of ultrasonic transducers forming a first ultrasonic transducer means for producing an ultrasonic beam, an ultrasonic transducer forming a second ultrasonic transducer means, the second ultrasonic transducer means being spaced from the first ultrasonic transducer means and serving to receive reflected ultrasonic waves, the transducer means being orientated such that there is a point of convergence between the axis of the ultrasonic beam produced by the first transducer means and the axis of the line of sight along which the second transducer means receives reflected waves, means for mounting a surgical needle, the needle mounting means being such that the axis of a needle carried thereby intersects said point of convergence and is skew to the plane which contains said axis of the ultrasonic beam and said axis of said line of sight, means for detecting the attitude of said needle mounting means and producing an output signal, and means for processing said output signal and feeding it to said phased array thereby to excite said phased array so that constructive interference between the wavelets occurs along an axis which intersects the point of convergence between the axis of a needle carried by the needle mounting means and the line of sight along which said ultrasonic transducer receives reflected ultrasonic waves.

6. A device according to claim 5, in which the means for detecting the attitude of the needle mounting means comprises a source of parallel light, a mirror carried by said needle mounting means for reflecting light from said source along a path which shifts upon there being a change in the attitude of said needle mounting means, and a light sensitive optical array for detecting where the light reflected from said mirror impinges thereon and for producing an output signal in dependance on the detected point of impingement.

7. A device according to claim 5, in which the means for detecting the attitude of the needle mounting means comprises magnetic means for producing an output signal in dependance on the detected attitude of the needle mounting means.

* * * * *